United States Patent [19]

Gautier et al.

[11] Patent Number: 4,661,608

[45] Date of Patent: Apr. 28, 1987

[54] PROCESS FOR THE MANUFACTURE OF SILYLMETALLOCENE COMPOUNDS

[75] Inventors: Jean-Claude C. Gautier, Ablon sur Seine; Serge F. Raynal, Draveil, both of France

[73] Assignee: Societe Nationale des Poudres et Explosifs, Paris, France

[21] Appl. No.: 749,803

[22] Filed: Jun. 28, 1985

[30] Foreign Application Priority Data

Jul. 20, 1984 [FR] France ................... 84 11506

[51] Int. Cl.$^4$ .................... C07F 17/02; C07F 17/00
[52] U.S. Cl. ........................................ 556/11
[58] Field of Search ............................ 556/11

[56] References Cited

U.S. PATENT DOCUMENTS

| | | | |
|---|---|---|---|
| 3,313,835 | 4/1967 | Wilkus et al. | 556/11 |
| 3,321,501 | 5/1967 | Wilkus et al. | 556/11 |
| 3,414,597 | 12/1968 | Wilkus et al. | 556/11 |

*Primary Examiner*—Helen M. S. Sneed
*Attorney, Agent, or Firm*—Cushman, Darby & Cushman

[57] ABSTRACT

The present invention relates to a process for the manufacture of silylmetallocene compounds and the compounds obtained by this process.

The process of the invention consists in reacting, in the presence of a hydrosilylation catalyst, a metallocene of general formula (I):

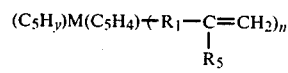

M denoting a transition metal such as iron with a halosilane of general formula (II):

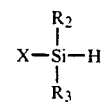

in which X denotes a halogen and then reducing the resultant product to form a silylmetallocene compound containing at least one Si-H bond.

The invention has application in the field of chemical industry.

9 Claims, No Drawings

PROCESS FOR THE MANUFACTURE OF SILYLMETALLOCENE COMPOUNDS

The present invention relates to a process for the manufacture of silylmetallocene compounds, and compounds obtained by this process.

The invention refers more particularly to a process of synthesis by hydrosilylation of a metallocene compound containing at least one substituent consisting of a silylidene radical.

The metallocene compounds, such as dicyclopentadienyl iron, called ferrocene, are known and employed in various applications such as, for example, as a combustion catalyst or antioxidant.

It has been found that their properties are improved by the addition of organosilyl radicals bound directly by carbon-silicon bonds to the cyclopentadienyl nucleus of the metallocene. Such compounds are described, particularly in French Pat. Nos. 1,396,273, 1,456,277, 1,398,255 and 1,396,272.

To synthesize these products, several processes have already been proposed, described, in particular, in the abovementioned French patents. Thus, French Pat. No. 1,398,255 describes a process for obtaining an organosilylmetallocene employing a reaction of acylation of the metallocene using a silylcarboxylic acid halide, the carbonyl group being then reduced to a methylene radical. French Pat. No. 1,456,277 also describes a process employing magnesium compounds to obtain silylmetallocenes. For this purpose, the Grignard reagent of a haloarylmetallocene is reacted with a halide, the haloarylmetallocene Grignard reagent being obtained either by the process described by William F. Little et al., Journal of Organic Chemistry, Vol. 20, p. 213 of March 1964, or by the operating procedure of Victor Weinmayer, Journal of the Americal Chemical Society, 77, 3012 (1955).

These known processes make it possible to synthesize the silylmetallocene in low yields, approximately 20% for the acylation reaction and 10% for the process using a magnesium compound.

In addition, the starting materials employed in these two syntheses are not commercially available; it is necessary therefore, even before synthesizing the silylmetallocene, to manufacture the silylcarboxylic acid halide or the Grignard reagent of a haloarylmetallocene, which further reduces the overall yield of the reaction and increases the prime cost of the silylmetallocene.

The aim of the present invention is to overcome these disadvantages by offering a process for the manufacture of a silylmetallocene compound employing commercially available starting materials and with subsequent reactions having a high overall yield.

To this end, the invention offers a process for the manufacture of a silylmetallocene compound containing at least one metallocene radical and at least one silylidene radical, consisting:

in reacting, in the presence of a hydrosilylation catalyst, a metallocene of the following general formula (I)

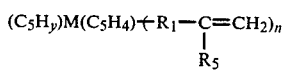  (I)

in which:
M is a transition metal included in the group comprising iron, osmium, ruthenium, nickel, cobalt, manganese and titanium;
$R_1$, which need not be present, denotes a saturated or unsaturated, substituted or unsubstituted aliphatic radical, a substituted or unsubstituted aromatic radical, or a substituted or unsubstituted alkenylcarbonyl radical;
$R_5$ denotes hydrogen, or a substituted or unsubstituted aliphatic or aromatic radical;
n is equal to 1 or 2; y is equal to $5-(n-1)$; with a halosilane of the following general formula (II):

  (II)

in which:
X denotes a halogen chosen from the group consisting of chlorine, bromine and iodine;
$R_2$ and $R_3$, which may be identical or different, denote hydrogen, a substituted or unsubstituted aliphatic radical or a substituted or unsubstituted aromatic radical;
in reducing the resultant product to form the silylmetallocene compound and in extracting the said compound from the reaction medium.

The silylmetallocene compound obtained by the process of the invention has one of the following general formulae (III, IV):

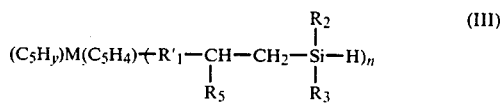  (III)

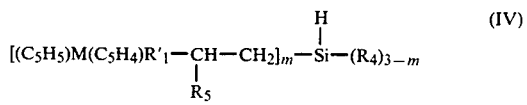  (IV)

x, y, n, $R_2$ and $R_3$ having the meanings indicated above;
$R_4$ having the meaning of $R_2$ or $R_3$;
$R'_1$ is a branched or unbranched alkenyl chain, or an aromatic chain, obtained by hydrogenation of the radical denoted by $R_1$ in formula I;
m is equal to 1, 2 or 3.

According to another characteristic of the invention, the metallocene of formula I and the halosilane of formula II are added in a common solvent.

The solvents which are particularly suitable for the invention are benzene, toluene, tetrahydrofuran or a mixture thereof.

Of course, the invention is not restricted to the solvents indicated above. Thus, the compounds in which the metallocene and the halosilane are soluble may be employed as suitable solvents for the invention.

According to another characteristic of the invention, the reduction reaction of the silyl radical and of the carbonyl groups, when they are present, is carried out in the same solvent as that employed for the hydrosilylation reaction, and advantageously in the reaction medium resulting from the latter reaction.

According to yet another characteristic of the invention, the hydrosilylation reaction is carried out in a heterogeneous medium, without solvent, the subsequent reduction reaction being then preferably carried out in an ether solvent.

The hydrosilylation reaction is carried out in the presence of a hydrosilylation catalyst chosen from the group comprising $H_2PtCl_6$, platinum, and nickel or cobalt salts. Hexachloroplatinic acid is the preferred catalyst. The reaction temperature is between approximately $-5°$ C. and approximately $90°$ C. This temperature is determined by the boiling point of the solvent chosen.

Advantageously, the halosilane of formula II is added in an excess relative to the stoichiometric quantity, so as to have a ratio of the numbers of Si—H bonds in the halosilane, to the number of vinyl bonds present in the metallocene of formula I, which equals at least 2.

The reduction reaction is also carried out in the presence of a hydrogenation catalyst such as, for example, $LiAlH_4$.

Extraction of the synthesized silylmetallocene compound is carried out by any suitable methods such as evaporation, distillation, solvent extraction or similar.

Preferably, the silylmetallocene is extracted from the reaction medium with a solvent, the latter being then evaporated off.

In the preferred embodiment of the invention the radicals, $R_2$, $R_3$ and $R_4$ in the general formulae III and IV are methyl or ethyl radicals, while the radical $R'_1$, when it exists, is a methylenic chain containing from 1 to 10 carbon atoms.

The preferred metallocene of the invention is ferrocene of formula $[(C_5H_5)Fe(C_5H_4)]$, denoted below by the symbol Fc.

The following examples, given solely by way of indication, illustrate the invention more clearly.

EXAMPLE 1

Synthesis of dimethylsilyldimethyllleneferrocene:

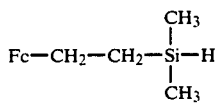

75 mg of $H_2PtCl_6.6H_2O$ are introduced into 12 g of dimethylchlorosilane under a nitrogen atmosphere. The mixture is heated under reflux until the hexachloroplatinic acid has dissolved completely.

A solution of 12.72 g of vinylferrocene in 45 ml of benzene is added to the reaction medium, the temperature of the reaction medium being below $38°$ C.

The ratio of the Si—H bonds to the vinyl bonds is 2.08.

The reaction mixture is kept at a temperature of $34°$ C. with stirring for 5 hours.

The excess dimethylchlorosilane and benzene are then evaporated off.

The residue is dissolved in anhydrous ether and added slowly to a suspension of $LiAlH_4$ in anhydrous ether heated under reflux. The heating is continued for 48 hours. After cooling, excess lithium aluminium hydride is hydrolysed with water-saturated ether, and then with water.

The silylferrocene is then extracted with ether from the reaction medium. After drying and evaporation of the solvent, a brown liquid residue is collected, which is analysed by column chromatography.

In this way 12 g of 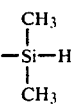 are obtained, i.e. a weight yield of 74% based on the vinylferrocene employed.

EXAMPLE 2

Synthesis of dimethylsilyltetramethyleneferrocene:

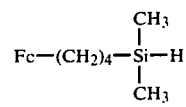

The operation is carried out using the same procedure as before, but with the use of 4-butanylferrocene as the starting ferrocene compound. Dimethylsilyltetramethyleneferrocene is obtained in a weight yield of 50%.

EXAMPLE 3

Synthesis of dimethylsilylisopropylferrocene:

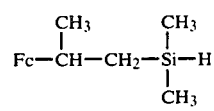

This operation is also carried out according to the procedure of Example 1, with the exception that vinylferrocene is replaced by 1-methylvinylferrocene.

A brown liquid product is also obtained.

EXAMPLE 4

The operating procedure of Example 1 is carried out, the difference being that 1,3-butadienylferrocene is added instead of vinylferrocene.

A mixture of two silylferrocenes is then obtained:
dimethylsilyltetramethyleneferrocene,
2-dimethylsilyl-1-ferrocenebutane.

The overall yield of the reaction is of the order of 20% in this example.

EXAMPLE 5

The compound

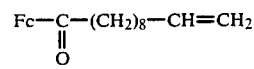

is first prepared by reacting a ferrocene and the acid chloride

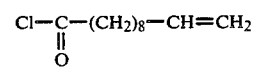

in dichloromethane and in the presence of $AlCl_3$.

After hydrolysis of $AlCl_3$, the compound

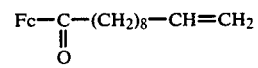

is extracted and reacted with dimethylchlorosilane in accordance with the operating procedure described in Example 1.

Dimethylsilylundecamethyleneferrocene is obtained.

The various products synthesized have been identified by infrared analysis and, more particularly, the Si—H bond has been characterized.

The examples given above show the general application of the process of the invention for all metallocene compounds containing a substituent with a double bond.

The silylmetallocenes produced by the process of the invention have many applications which are described, for example, in French Pat. No. 1,396,273 of May 27 1964. Thus, they may be employed for the manufacture of polymers, the removal of smoke, the acceleration of the vulcanization of rubbers, as adjuvants for diesel fuels and as combustion catalysts, for example.

We claim:

1. A process for the manufacture of a silylmetallocene compound containing at least one metallocene radical and at least one silylidene radical comprising (a) reacting, in the presence of a hydrosilylation catalyst, a metallocene having the formula:

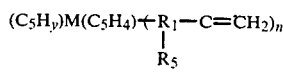

wherein

M is a transition metal selected from the group consisting of iron, osmium, ruthenium, nickel, cobalt, manganese and titanium, $R_1$, which need not be present, represents a saturated or unsaturated aliphatic radical, an aromatic radical or an alkenylcarbonyl radical, $R_5$ represents hydrogen, an aliphatic radical or an aromatic radical, n is equal to 1 or 2 and y is equal to $5-(n-1)$, with a halosilane of the formula

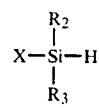

wherein

X represents a halogen selected from the group consisting of chlorine, bromine and iodine, $R_2$ and $R_3$ each independently represent hydrogen, an aliphatic radical or an aromatic radical, (b) reducing the product of step (a) in the presence of a hydrogenation catalyst so as to form said silylmetallocene compound, and (c) extracting said silylmetallocene compound from the reaction medium.

2. The process of claim 1 wherein said halosilane and said metallocene are added in a common solvent selected from the group consisting of benzene, toluene, tetrahydrofuran and mixtures thereof.

3. The process of claim 2 wherein the reduction reaction of step (b) is carried out in said common solvent employed for the hydrosilylation reaction of step (a).

4. The process of claim 1 wherein the hydrosilylation reaction of step (a) is carried out in a heterogeneous medium.

5. The process of claim 1 wherein the reduction reaction of step (b) is carried out in an ether solvent.

6. The process of claim 1 wherein the hydrosilylation reaction of step (a) is carried out at temperature between $-5°$ C. and $+90°$ C.

7. The process of claim 1 wherein said halosilane is added in excess to have a ratio of the Si—H bonds of the halosilane to the vinyl bonds carried by the metallocene equal to at least 2.

8. The process of claim 1 wherein said halosilane is dimethylchlorosilane.

9. The process of claim 1 wherein said metallocene is vinylalkenylferrocene.

* * * * *